US009662653B2

(12) United States Patent
Spangler

(10) Patent No.: US 9,662,653 B2
(45) **Date of Patent: *May 30, 2017**

(54) THERMAL ARRAY AND METHOD OF USE

(71) Applicant: Frank Leo Spangler, St. George, UT (US)

(72) Inventor: Frank Leo Spangler, St. George, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/846,931

(22) Filed: Sep. 7, 2015

(65) Prior Publication Data

US 2015/0375230 A1 Dec. 31, 2015

Related U.S. Application Data

(63) Continuation-in-part of application No. 12/697,184, filed on Jan. 29, 2010, now Pat. No. 9,399,219.

(51) Int. Cl.
*C12M 1/34* (2006.01)
*B01L 7/00* (2006.01)

(52) U.S. Cl.
CPC ..... *B01L 7/5255* (2013.01); *B01L 2300/0809* (2013.01); *B01L 2300/1805* (2013.01); *B01L 2300/1822* (2013.01); *B01L 2300/1827* (2013.01); *B01L 2300/1883* (2013.01)

(58) Field of Classification Search
CPC ........... B01L 7/5255; B01L 2300/1805; B01L 2300/1822; B01L 2300/1827; B01L 2300/1883; H05B 3/68; H05B 3/70; H01L 35/34; H01L 21/67103
See application file for complete search history.

(56) References Cited

U.S. PATENT DOCUMENTS 4,740,664 A * 4/1988 Payne .................... G05D 23/24 219/448.12
4,810,857 A * 3/1989 Goessler ................ H05B 3/746 219/448.19
2007/0278206 A1* 12/2007 Pittman .................... A45D 2/00 219/225

FOREIGN PATENT DOCUMENTS

CN WO 2008062293 A1 * 5/2008 ............... A45D 1/04
DE 2335257 A1 * 1/1975 .............. F24C 15/10
GB 2459507 A * 10/2009 ............... A45D 1/04

OTHER PUBLICATIONS

English language maching translation of DE 2335257 (Jan. 1975) (2 pages).*

* cited by examiner

*Primary Examiner* — William H Beisner
(74) *Attorney, Agent, or Firm* — Gallian, Welker & Beckstrom, L.C.; Robert A. Gurr

(57) ABSTRACT

In one embodiment, a thermal array comprises a first heating element and a second heating element, each surrounded by insulators which cover five sides of each heating element, held in position by a cooling block. Two thermal arrays are placed opposite each other creating a conduction channel wherein a sample vessel is transported between the heating elements and cooling block as the reaction requires. Due to the low energy consumption of each array, the thermal array system may function using standard D-cell batteries.

13 Claims, 6 Drawing Sheets

THERMAL ARRAY AND METHOD OF USE

RELATED APPLICATIONS

This application is a continuation-in-part of prior non-provisional application Ser. No. 12/697,184, filed Jan. 29, 2010, titled THERMAL ARRAY, and incorporated herein by reference.

TECHNICAL FIELD

The present application relates to biotechnology. More particularly, the present application relates to portable polymerase chain reaction (PCR) devices.

BACKGROUND

Since its invention, the polymerase chain reaction (U.S. Pat. No. 4,683,202) has become a powerful force in biotechnology. It is a method to exponentially amplify essentially exact copies of a DNA segment. DNA is a double stranded molecule that when heated to temperatures such as 95° C., will dissociate into two separate strands. Using small synthetic DNA fragments called primers that can complementary base pair to the dissociated DNA strands at temperatures such as 45-65° C., the primers anneal to the template DNA. Finally, elongation takes place at around 72° C. using an enzyme called a DNA polymerase to extend off of one end of the primer by adding complementary nucleotides (dNTP's) to the extant original template DNA—making a new copy strand of DNA. Both of these two DNA strands are used in subsequent PCR cycles as templates along with the annealed primers to make two new copy strands of DNA for a total of four strands, which are called elongation events. By repeating the cycle of dissociating, annealing and elongating the reaction again, there is a doubling of new DNA strands produced. Repeat the cycle over 30 times and theoretically there are billions of exact DNA copies in the reaction vessel. These heating and cooling cycles, along with the template DNA, primers, dNTP's and DNA polymerase, are what constitute the PCR method. PCR is usually performed in automated devices that thermocycle the temperatures needed for the production of amplification products after all of the template DNA, primers, dNTP's and enzyme have been added to a sample vessel.

Conventional PCR devices, such as Peltier thermoelectric devices like the AB 9700 (U.S. Pat. No. 7,133,726 B1), convection heat exchangers like the Roche LightCycler (Wittwer, C. T., et al., Anal. Biochem. 186: p 328-331 (1990) and U.S. Pat. No. 5,455,175) and the like, are typically power hungry, take a while to complete a run, and/or are difficult to transport. All these PCR devices must thermal cycle in order to heat and cool the sample vessels they hold. The 9700 does this by constructing its sample holder out of a big block of metal and pumping heat energy into and out of the system through thermal conduction. Electrical energy is required both to add heat energy to the sample block and to remove heat energy from the block. This requires a lot of electrical energy due to the large mass of the sample block. For example, the AB 7500 consumes approximately 1,080 Watts during a run. The LightCycler avoids the large sample block by using thin capillary tubes with relatively small masses and cycles the temperature by convection with heated air. Like the 7500, the heating element in the LightCycler uses a lot of electrical energy.

Most of these devices are designed to be setup in a laboratory environment and not moved from location to location because they are large and heavy. Moving such devices typically requires a strong person, or a sturdy-wheeled vehicle such as a reinforced wagon or handcart. Further, it is common that these devices require a standard 120V to 250V outlet for power. Further, the devices cannot readily be moved from room to room once inside a laboratory. For standard PCR devices like the AB 7500, the run time for 40 cycles is 60 minutes. By trying to run them faster, you reduce the efficiency of the PCR reaction, which means that the sensitivity of the reaction is reduced. Portable and fast PCR devices are needed, especially in fields like medical diagnostics, where a physician needs test results in 15-20 minutes in a point of care (POC) situation. Additionally, the cost of these traditional PCR thermal cyclers limits their application to R&D, medical labs, forensic and other testing facilities. One market that is completely underserved due to cost, is education. A small, rapid, and low cost PCR device would allow high schools, small business labs, and smaller colleges the opportunity to finally perform testing and education that is currently cost prohibitive.

Prior art (Festoc, U.S. Pat. No. 6,821,771) described a heating plate having at least two zones for heating at two different temperatures. What this prior art failed to anticipate was the need to thermally isolate one heating element from another. By placing a higher temperature element in close proximity to a lower temperature element on a heating plate, a thermal gradient is created as described by Lurz (U.S. Pat. No. 6,767,512). The current disclosure solves this problem by adding sufficient insulating materials, which eliminates the thermal gradient and provides for proper thermal control for high efficiency biological reactions, such as PCR. Additionally, the prior art failed to anticipate the need for a cooling block to extract heat energy from a sample vessel when transitioning from a high temperature heating element to a lower temperature heating element. The current disclosure provides for a cooling block, which reduces the overall run time giving faster run results.

SUMMARY OF EXAMPLE EMBODIMENTS

The present disclosure is a low energy, small, lightweight, high-efficiency, and rapid thermal array comprising an insulated heating element, a cooling block which acts as a heat sink, and an insulated heating element placed in tandem. The thermal array completely eliminates the mass of the traditional sample block while maintaining the higher efficiency of heat transfer by conduction versus convection. The thermal array is in direct contact with a sample vessel throughout the process. This allows for greater control over thermal profile variations as there are no undershoots or overshoots of temperatures common to conventional PCR devices. Rather than converting electrical energy to heat energy, and adding heat energy to the device, and then transferring this energy to a sample block and finally to a sample vessel, the thermal array moves the sample vessel from one heating element to another heating element or cooling block without ramping the device from one temperature to another; in other words, it doesn't thermal cycle a sample block which is highly energy inefficient. Additionally, the heating element is insulated so no heat loss to the device or environment takes place. Heat energy is transferred only into the sample vessel in a unidirectional flow of heat energy, greatly enhancing the efficiency of the power budget for the thermal array and reducing the overall run times. The thermal array converts electrical energy, from either an AC or DC power source, into heat energy, and transfers it directly into the sample vessel without ramping the temperature. It is more efficient to bring each heating element to temperature and hold them at a target temperature than it is to continually raise and lower the temperature of a heating element—a process referred to as "ramping the temperature" and which is used by more traditional PCR devices. In the current disclosure, when going from a higher temperature heating element to a lower temperature heating element, the cooling block is used to extract the heat energy from the sample vessel, which further decreases the overall run time of the reaction. Because going from one temperature in a sample vessel to another temperature using the thermal array requires only a fraction of a second as the sample vessel is moved from one heating element to the next, thermal cycling of a sample vessel is extremely rapid. Traditional PCR devices have ramp rates of 1.0-2.5° C./sec. and rapid PCR devices have ramp rates of about 5.0° C./sec. Going from 60.0° C. to 95.0° C. could take anywhere from 7.0 to 35.0 seconds in a traditional PCR device while taking less than 0.5 seconds using a thermal array as disclosed herein. This leads to a marked decrease in the overall run-time of the thermal array device. A standard PCR device, like the AB 7500, uses sixty minutes or more to complete a single run. In one embodiment, the thermal array as disclosed herein, can complete the same efficiency run in less than twenty minutes. By using modified primers and optimized PCR conditions, the thermal array as disclosed herein can complete a run in less than eight minutes. Due to the simplification, a thermal array device as disclosed herein costs a fraction of what a traditional PCR device costs. This allows the thermal array device to go into markets that were previously cost prohibitive for traditional devices.

DETAILED DESCRIPTION OF EXAMPLE EMBODIMENTS

The following descriptions depict only example embodiments and are not to be considered limiting of its scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may.

Accordingly, the particular arrangements disclosed are meant to be illustrative only and not limiting as to the scope of the invention, which is to be given the full breadth of the claims and any and all equivalents thereof. Moreover, many embodiments, such as adaptations, variations, modifications, and equivalent arrangements, will be implicitly disclosed by the embodiments described herein and fall within the scope of the present invention. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various different sequences and arrangements while still falling within the scope of the present invention. Further, while the reactions required for PCR are discussed herein, the present invention is not limited to those reactions and may be used for other reactions and/or processes.

Figure 1:
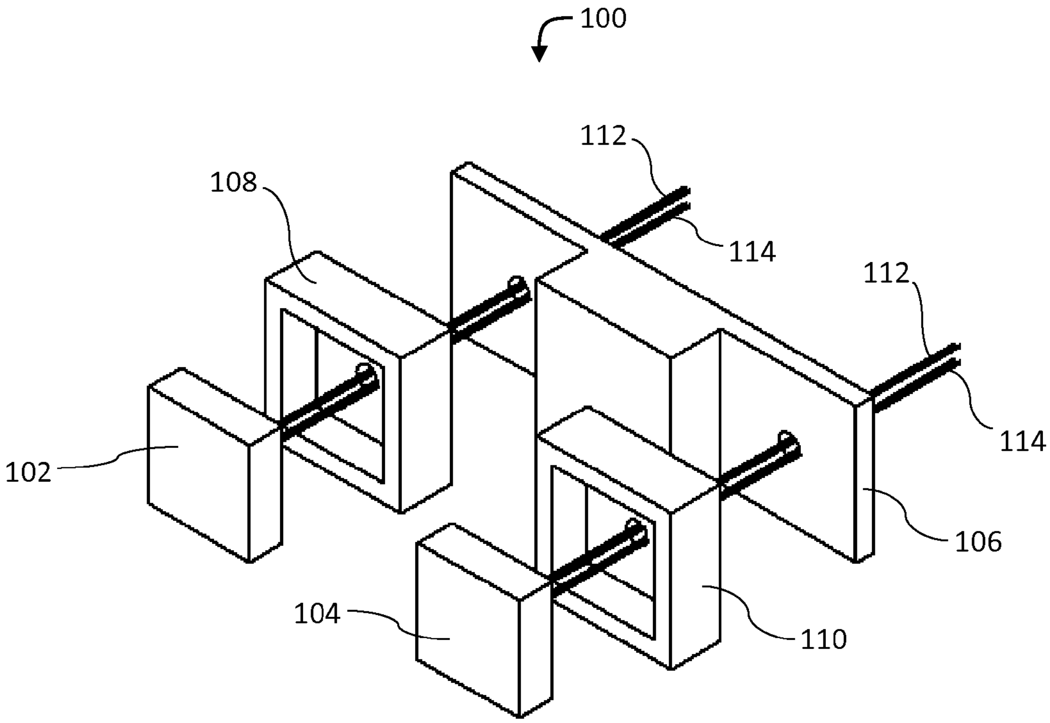
FIG. 1 is an exploded view of a thermal array.
Figure 2A:
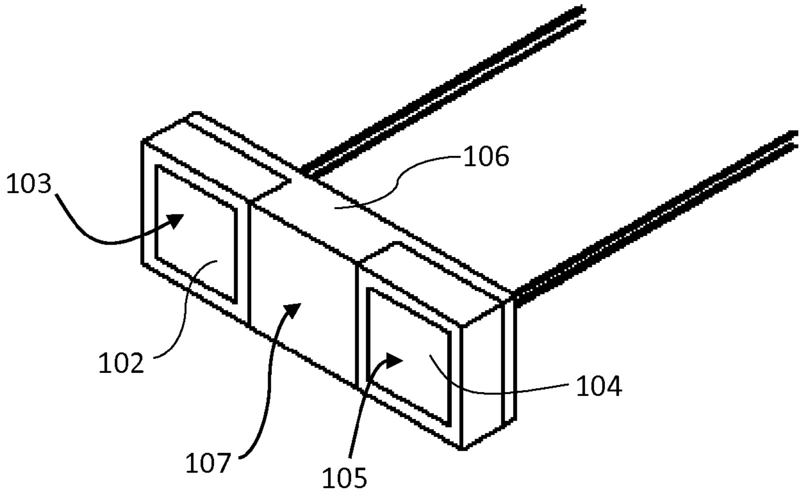
FIG. 2A is a front perspective view of a thermal array.
Figure 2B:
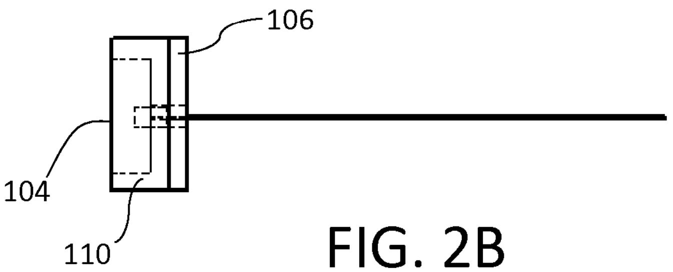
FIG. 2B is a side elevation view of a thermal array.
Figure 2C:
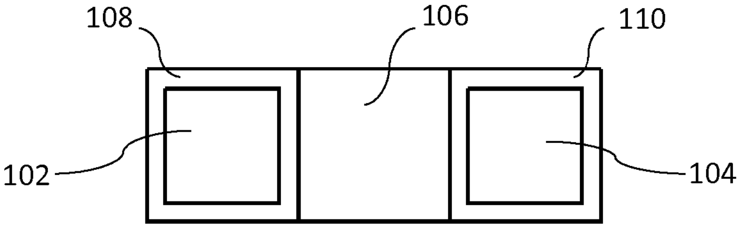
FIG. 2C is a front elevation view of a thermal array.
Figure 2D:
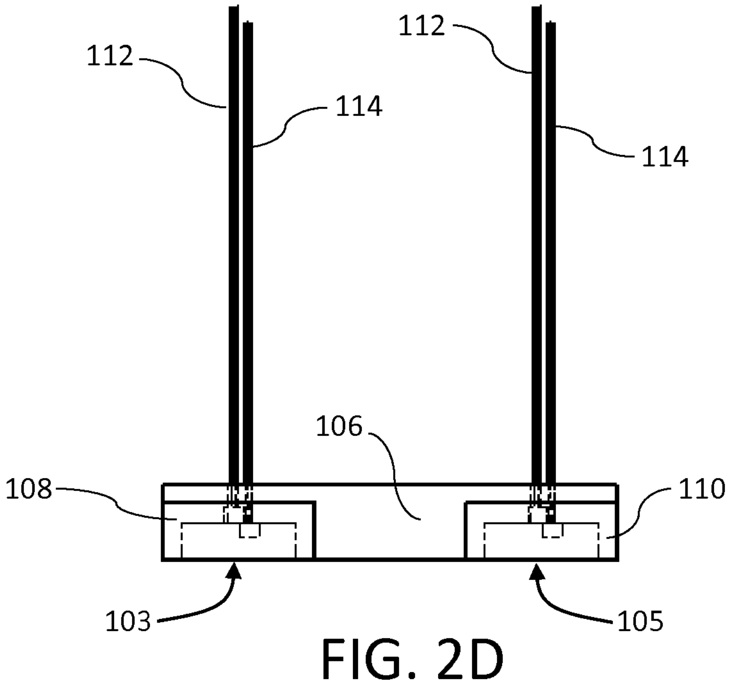
FIG. 2D is a top view of a thermal array.

Referring now to FIGS. 1 to 2D there is shown a thermal array 100 having a first heating element 102 and a second heating element 104 held in position by a cooling block 106. Each of the heating elements 102 and 104 are coupled or otherwise connected to the cooling block 106 with insulators 108 and 110 covering five sides of the heating elements 102 and 104. Each heating element 102, 104 has a temperature sensor (e.g., digital thermal sensor) connected via wire 112, and a power source, such as a battery, connected via wire 114 to generate the heat in the heating elements 102, 104. The cooling block 106 may be made from aluminum alloy, copper, some combination thereof, or any other material known in the art that functions well as a heat sink (i.e., draws heat from the source). The heating elements 102, 104 may be standard resistive heating elements known in the art, such as nickel-chromium (Nichrome) wire, or any equivalent. Insulators 108 and 110 are used to direct the flow of heat energy to the non-insulated surface and into a sample vessel.

Figure 3:
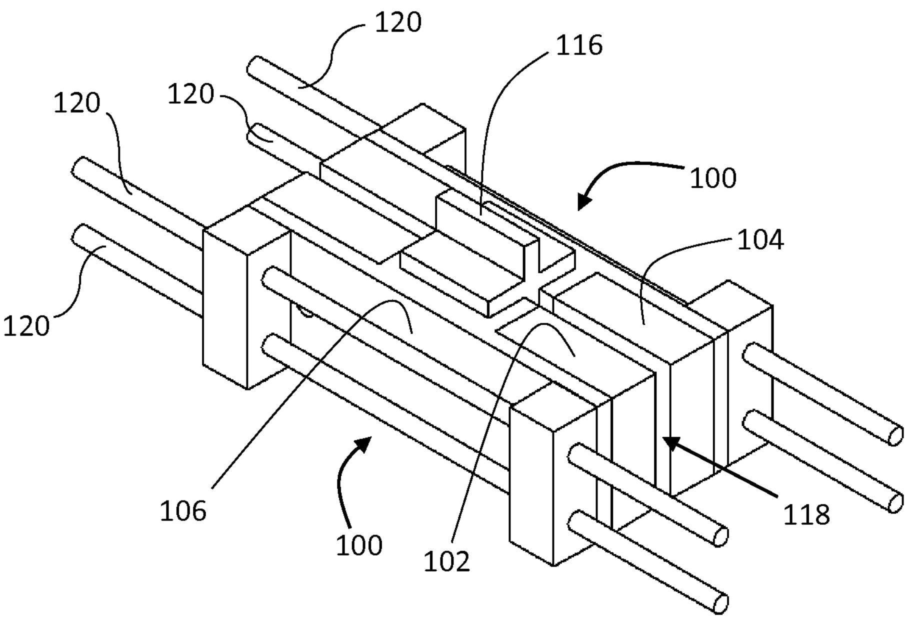
FIG. 3 is a perspective view of a thermal array system.
Figure 4:
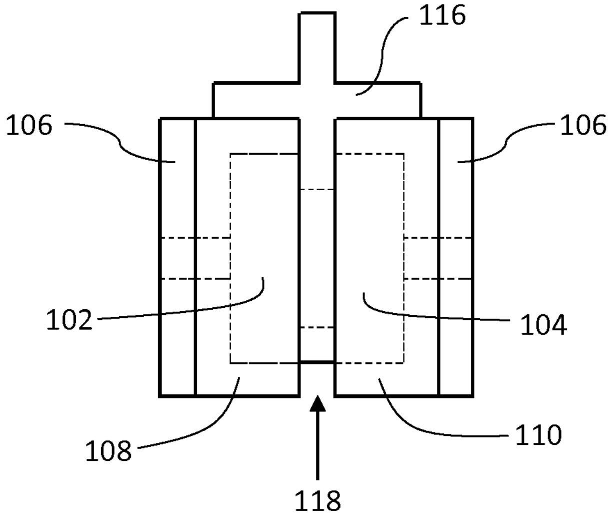
FIG. 4 is a side elevation view of a thermal array system.
Figure 5A:
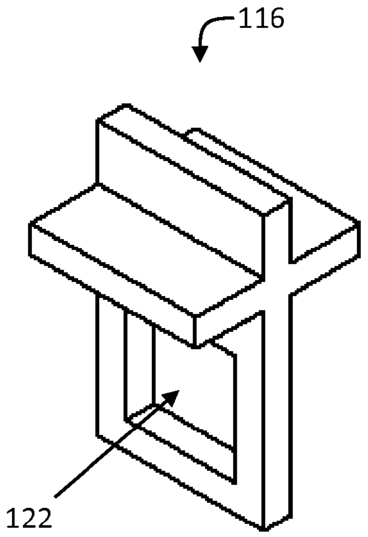
FIG. 5A is a perspective view of a sample vessel transporter of a thermal array system.
Figure 5B:
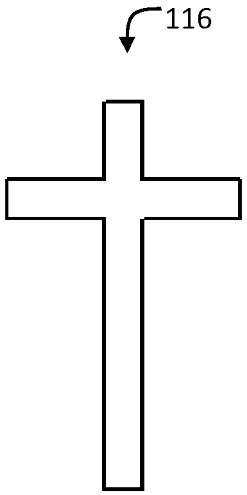
FIG. 5B is a side elevation view of a sample vessel transporter of a thermal array system.
Figure 5C:
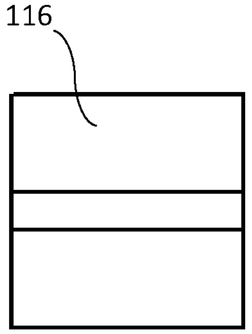
FIG. 5C is a top view of a sample vessel transporter of a thermal array system.
Figure 5D:
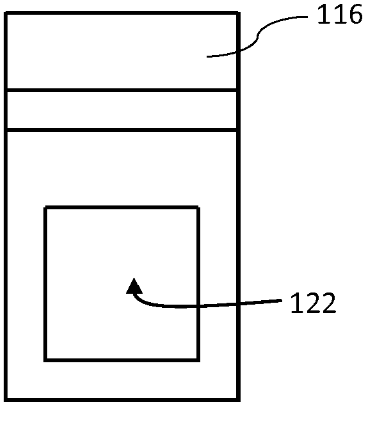
FIG. 5D is a front elevation view of a sample vessel transporter of a thermal array system.

The insulators 108 and 110 can be made of typical materials such as fiberglass, expanding spray foam, Aerogel, or any equivalent. The insulators 108 and 110 help prevent heat energy loss into other components of the thermal array 100 and the environment. Heat energy loss is power loss, which means more electrical energy would be required to complete a PCR run. However, as shown in FIGS. 2A-2D only the front side 103 and 105 of the heating elements 102 and 104 are exposed. Front sides 103, 105 conduct heat to a sample vessel as it comes into contact with each of them, respectively. The cooling block 106 also has a front side 107 in-line with the insulated heating elements 102, 104 that likewise comes into contact with a sample vessel. Each of these exposed surfaces form a flat planar surface that a sample vessel comes into direct physical contact with to allow heat transfer by conduction. An example of this is shown in FIG. 3, where two thermal arrays 100 are placed opposite one another with a sample vessel 116 resting there-between in the conductive channel 118. This arrangement is referred to herein as a thermal array system. The sample vessel 116 is ideally aligned so as to be proximal to the flat planar surface of the respective thermal arrays 100 so as to maximize surface contact area and thermal conduction, as best seen in FIG. 4. As shown, sample vessel 116 is in direct contact with heating elements 102 or 104. The sample vessel 116 is best seen in FIGS. 5A-5D and comprises an aperture 122, which allows for placement/insertion of a reaction mixture. For example, a thin film may be placed on each side of aperture 122, allowing for the containment of a reaction mixture therein. Various plastics, metals, or other thermally conductive materials may be used to allow the containment of the reaction mixture within aperture 122. This placement allows maximum contact of the reaction mixture with thermal arrays 100, as illustrated in FIGS. 3 and 4.

Returning to FIGS. 3 & 4, in one method of use of a thermal array system, a sample vessel 116 containing a reaction mixture is placed in conductive channel 118. As shown, the heating elements 102, 104 of the two thermal array devices are directly opposite one another, as are each of the cooling blocks 106. It will be noted that either thermal array may be rotated so that varying heating elements are opposite each other, and that the important factor is that the heating elements opposite each other have the same temperature. For the necessary reactions to occur, the sample vessel 116 is moved or moves from one pair of heating elements heated to a first temperature, to the cooling block, to a second pair of heating elements heated to a second temperature and then back again (or as the reaction requirements dictate). It is important to note that the heating elements 102, 104 do not change in temperature, but remain at a preset temperature for the reaction. It is further noted that the cooling block 106 is extremely useful in dropping the temperature of the sample vessel 116 very quickly, as may be needed for the reaction as well. Movement of the sample vessel 116 may be achieved in a variety of manners, such as by hand or by a stepper-motor or solenoid and using a set of guide rods 120 for stabilizing the thermal arrays 100 during such movement. The reaction mixture within sample vessel 116 is able to fluctuate in temperature very rapidly within the set of thermal arrays 100 due to the close proximity of the thermal arrays 100 and the ability of the same to control temperatures using the various heating elements 102 and 104, cooling block 106, and insulators 108 and 110. This makes reactions, such as those required for PCR, very quick to accomplish. As readily apparent, with each heating element 102, 104 within an insulator 108, 110, heat loss is minimized as is a heat gradient between the heating elements 102, 104 and the cooling block 106. Further, cooling block 106 allows heat to be withdrawn from the sample vessel 116 at a rapid rate, which increases the overall speed with which a reaction may be completed.

The thermal array 100 may be made from aluminum or of any other sufficiently rigid and strong material, such as high-strength plastic, metal, and the like that also allows for high efficiency thermal conductivity. The sample vessel insulators 108, 110 are comprised of material that allows the heating elements 102, 104 to be optimally thermally isolated from the cooling block 106 while still in physical contact with it.

Figure 6A:
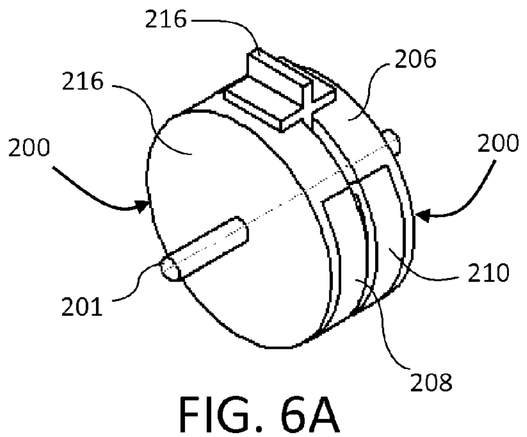
FIG. 6A is a perspective view of a thermal array system in a circular form factor.
Figure 6B:
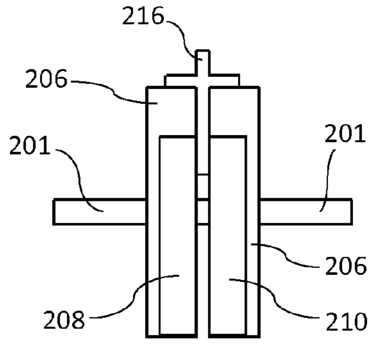
FIG. 6B is a side elevation view of a thermal array system in a circular form factor.
Figure 6C:
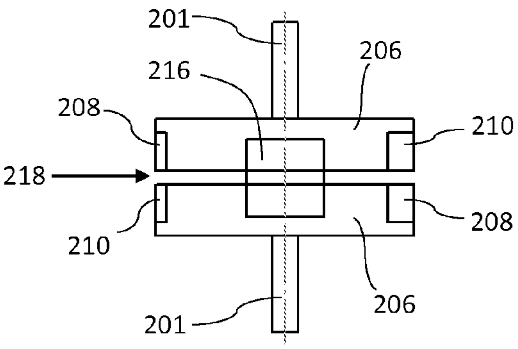
FIG. 6C is a top view of a thermal array system in a circular form factor.
Figure 6D:
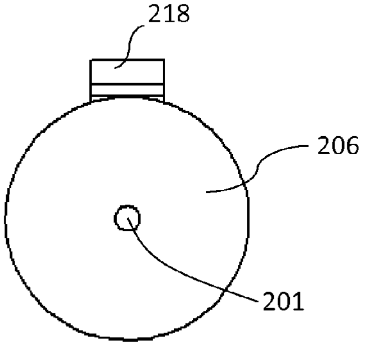
FIG. 6D is a front elevation view of a thermal array system in a circular form factor.
Figure 7:
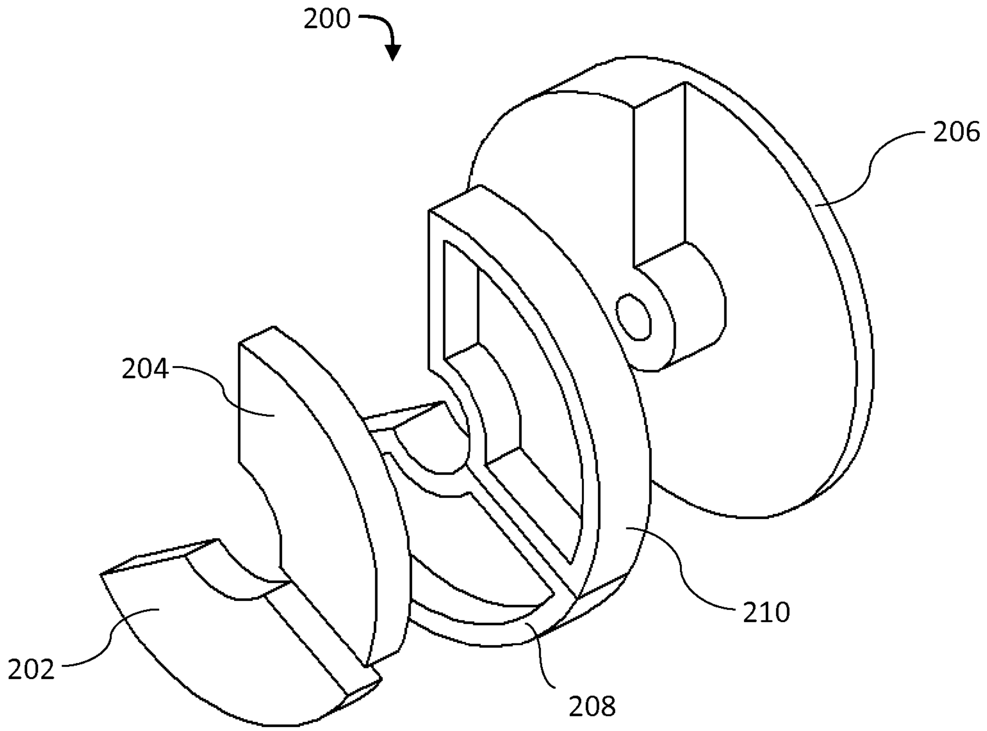
FIG. 7 is an exploded view of a thermal array in a circular form factor.

In another embodiment, as best shown in FIG. 7, a thermal array 200 is in a circular orientation. Thermal array 200 comprises insulated heating elements 202, 204, a cooling block 206, and insulators 208, 210. In one method of use, the thermal array 200 rotates around its axis 201 while a sample vessel 216 remains stationary, as seen in FIGS. 6A-6D.

For example, the thermal array 200 is placed opposite another thermal array 200 with a sample vessel 216 placed there-between. As best seen in FIG. 6B, the sample vessel 216 is proximal to, and in direct contact with, each of the thermal arrays 200, which creates a conductive channel 218. The thermal array 200 may be moved by the use of a stepper-motor (or equivalent means) rotating around the thermal array's axis 201 to bring the sample vessel 216 into direct contact with the various heating elements 202, 204 or cooling block 206, respectively.

As with previous embodiments, the thermal array 200 may be comprised of aluminum or of any other sufficiently rigid and strong material such as high-strength plastic, metal, and the like that also allows for high-efficiency thermal conductivity. The sample vessel insulators 208, 210 are comprised of material that allows the heating elements 202, 204 to be optimally thermally isolated from the cooling block 206 while still in physical contact with it.

Traditional PCR devices change the temperature of a sample vessel by converting electrical energy into heat energy, transferring the heat energy to the device and finally transferring the heat energy to a sample vessel by conduction, convection, or radiation. Most of the power budget or total Watts of electrical energy consumed during a PCR run in traditional devices is in ramping from one temperature to another temperature. Maintaining an insulated heating element, as disclosed herein, at a target temperature requires a fraction of the amount of electrical energy that is spent ramping the heating element to that temperature by pulsing the heating element with electrical energy by means of pulse width modulation as is known in the art. Generally speaking, the faster the temperature ramp rate, the more electrical energy required to reach the target temperature. All of the electrical energy used to transition from one temperature to another is lost to the system because little to no biological activity is taking place in a sample vessel during thermal ramping. A thermal array as disclosed herein does not waste any electrical energy ramping the device from one temperature to another. It has distinct heating elements and moves the sample vessel between them. Essentially all of the heat energy produced by the thermal array is transferred directly into a sample vessel, greatly reducing the power budget of the thermal array to complete a PCR run. Because of this reduced need for power, the currently disclosed thermal arrays can function using either AC or DC power. In other words, the thermal arrays as disclosed herein can function using 6-18 volt batteries. This is an important improvement over the prior art. Because this device is low energy, high efficiency, very rapid, and very portable, it is capable of running on batteries for days to weeks at a time. For example, four D-cell batteries have enough power to drive the 95° C. insulated heating element for approximately 28 hours. As is known in the art, by increasing the voltage potential of the battery, say from 6 volts to 48 volts, the current required to generate the same amount of heat energy drops. The batteries last longer because less current is being used for each run. Other attempts at making a portable PCR device have concentrated on shrinking traditional PCR device technologies into a smaller package. However, by fundamentally changing how the sample is processed, the thermal array and thermal array system as disclosed herein allow heretofore unseen achievements in portability, speed of runs, and power budget efficiencies. By greatly simplifying the technology, the cost to manufacture this technology has also reached unheard of low levels.

It is readily apparent that the advantages of the present invention include, without limitation, that it is portable and exceedingly easy to transport. It is easy to move these devices into and around a laboratory, school, or medical office because they are relatively small and lightweight. Moving such a device typically requires a single person. The thermal array can easily be powered by an AC to DC power supply in the 6-18 volt range. Further in a preferred implementation, because of the greater efficiency of a thermal array, the thermal array devices can function using batteries that can be recharged by an AC to DC power supply. Further, the devices can easily be moved out into the field to locations where services are needed—sometimes called point-of-care (POC) or point-of-service (POS). Further, the embodiments disclosed herein eliminate ramp times during a PCR run so the overall run times can be less than 8 minutes, versus the 60 minutes or so that is typical of conventional devices currently known in the art. Further, the simplification of the technology allows the thermal array as disclosed herein to be manufactured far below the costs of traditional PCR devices. Further, by increasing the voltage of the battery to, for example, 48 volts, the current required to produce the same amount of heat in the heating element drops. Using less current means that more PCR runs can be completed off of a single charge.

As disclosed herein, the cooling block can be either passive or made active by chilling it with various refrigeration technologies, such as, by way of example only, a Peltier element or cooling fins with or without a fan blowing over the fins. Fins are well known in the art and used frequently with heat sinks on computer CPUs and other heat sensitive components. Since the cooling block is a heat sink, by increasing the mass of the cooling block relative to the sample vessel, the overall cooling capacity of the cooling block can be increased. However, this increases the size and weight of the thermal array device. On the other hand, by actively cooling the cooling block, the size and weight of the thermal array can be decreased with a corresponding increase in the power budget. The junctions between each block are thermally insulated from the other. Small masses can be added to the exposed surfaces of the insulated heating elements to help stabilize temperature fluctuations. Additional insulated heating elements or cooling blocks may be added to the thermal array as needed. The thermal array allows sample vessel temperature changes to take place in a fraction of a second, thus decreasing overall reaction run times. Traditional PCR devices have ramp rates of 1.0-2.5° C./sec. and rapid PCR devices have ramp rates of about 5.0° C./sec. Going from 60.0° C. to 95.0° C. could take anywhere from 7.0 to 35.0 seconds in a traditional PCR device while taking less than 0.5 seconds using a thermal array system as disclosed herein. This leads to a marked decrease in the overall run-time of the thermal array device. A standard PCR device, like the AB 7500, uses 60 minutes or more to complete a single run. In one embodiment, the thermal array and thermal array system as disclosed herein can complete the same efficiency run in less than 20 minutes. By using modified primers and optimized PCR conditions, the thermal array can complete a run in less than 8 minutes.

What is claimed is:

1. A thermal array, comprising:

a first heating element having a front side exposed, the remaining sides covered by insulation; a second heating element having a front side exposed, the remaining sides covered by insulation, a cooling block coupled to, and interposed between, the first and second heating elements, the cooling block having a front side exposed and in the same geometric plane as the front sides of the first and second heating elements, the cooling block extending to cover the back side of each heating element.

2. The thermal array of claim 1, wherein the insulation is fiberglass.

3. The thermal array of claim 1, wherein the insulation is Aerogel.

4. The thermal array of claim 1, further comprising at least one temperature sensor.

5. The thermal array of claim 1, further comprising a Peltier element.

6. The thermal array of claim 1, wherein the cooling block is active.

7. The thermal array of claim 1, further comprising more than two heating elements, wherein the cooling block is interposed between, and extends behind, each heating element.

8. A thermal array system, comprising:

a first thermal array opposite a second thermal array creating a conductive channel, wherein each thermal array comprises at least one heating element having a front side exposed, with the remaining sides covered by an insulator with at least one insulated side being coupled to a cooling block; and a sample vessel receivable within the conductive channel that is proximate to, and in contact with, each thermal array.

9. A method of using the thermal array system of claim 8, comprising:

placing a reaction mixture in a sample vessel;

interposing the sample vessel between the first and second thermal arrays such that the sample vessel is proximate to, and in direct contact with, each thermal array; and alternating the position of the sample vessel, within the conductive channel, between at least one heating element and the cooling block of the thermal arrays so as to obtain the desired temperatures and results.

10. The method of using the thermal array system of claim 9, further comprising using batteries to power the heating elements.

11. The method of using the thermal array system of claim 10, wherein at least one battery is in a range from 6 Volts to 48 Volts.

12. The method of claim 9, further comprising a motor or solenoid as the means for alternating the position of the sample vessel.

13. The method of claim 9, further comprising a motor or solenoid as the means for alternating the position of the thermal array.

* * * * *